US 9,140,554 B2
(12) United States Patent
Jerauld

(10) Patent No.: US 9,140,554 B2
(45) Date of Patent: Sep. 22, 2015

(54) AUDIO NAVIGATION ASSISTANCE

(71) Applicant: Robert Jerauld, Kirkland, WA (US)

(72) Inventor: Robert Jerauld, Kirkland, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 38 days.

(21) Appl. No.: 14/163,943

(22) Filed: Jan. 24, 2014

(65) Prior Publication Data

US 2015/0211858 A1    Jul. 30, 2015

(51) Int. Cl.
G01C 21/00    (2006.01)

(52) U.S. Cl.
CPC ........................... G01C 21/00 (2013.01)

(58) Field of Classification Search
None
See application file for complete search history.

(56) References Cited

U.S. PATENT DOCUMENTS

| 6,323,807 | B1 | 11/2001 | Golding et al. |
| 6,456,438 | B1* | 9/2002 | Lee et al. ................. 359/630 |
| 7,598,927 | B2* | 10/2009 | Yamazaki et al. .......... 345/7 |
| 2003/0014186 | A1* | 1/2003 | Adams et al. ............. 701/207 |
| 2003/0179133 | A1* | 9/2003 | Pepin et al. .............. 342/357.08 |
| 2007/0016425 | A1 | 1/2007 | Ward |
| 2010/0241350 | A1* | 9/2010 | Cioffi et al. .............. 701/201 |
| 2012/0127284 | A1* | 5/2012 | Bar-Zeev et al. ........... 348/53 |
| 2012/0143495 | A1 | 6/2012 | Dantu |
| 2012/0212499 | A1* | 8/2012 | Haddick et al. ........... 345/589 |
| 2012/0268563 | A1* | 10/2012 | Chou et al. .............. 348/46 |
| 2013/0088726 | A1* | 4/2013 | Goyal et al. .............. 356/634 |
| 2013/0131985 | A1 | 5/2013 | Weiland et al. |
| 2013/0216093 | A1 | 8/2013 | Lee et al. |
| 2013/0278631 | A1* | 10/2013 | Border et al. ............. 345/633 |
| 2013/0328927 | A1* | 12/2013 | Mount et al. ............. 345/633 |
| 2014/0159862 | A1* | 6/2014 | Yang et al. .............. 340/5.52 |
| 2014/0168349 | A1* | 6/2014 | Eom et al. ............... 348/14.03 |
| 2014/0184384 | A1* | 7/2014 | Zhu et al. ................ 340/4.12 |
| 2014/0347265 | A1* | 11/2014 | Aimone et al. ............ 345/156 |

FOREIGN PATENT DOCUMENTS

WO    2012114123 A1    8/2012

OTHER PUBLICATIONS

Hub, Andreas et al., "Design and Development of an Indoor Navigation and Object Identification System for the Blind", Proceedings of the 6th International ACM SIGACCESS Conference on Computers and Accessibility, Oct. 18, 2004, 6 pages.

(Continued)

*Primary Examiner* — Calvin Cheung
(74) *Attorney, Agent, or Firm* — Sandy Swain; Judy Yee; Micky Minhas

(57) ABSTRACT

Embodiments that relate to a head-mounted computing device for providing navigation assistance via audio output are disclosed. For example, in one disclosed embodiment depth image and visible image data are used to generate a three-dimensional mesh of at least a portion of an environment. Using the mesh, at least one feature in the environment is detected. When operating in a familiar navigation mode and based on detecting the feature, a first audio navigation cue is outputted to the user. When operating in an unfamiliar navigation mode and based on detecting the feature, a second audio navigation cue is outputted to the user, where the second audio navigation cue differs from the first audio navigation cue.

20 Claims, 9 Drawing Sheets

(56) References Cited

OTHER PUBLICATIONS

Johnson, Maggie, "Google Research Awards: Summer 2013", http://googleresearch.blogspot.in/2013/08/google-research-awards-summer-2013.html#!/2013/08/google-research-awards-summer-2013.html, Aug. 13, 2013, 1 page.

Mann, Steve et al., "Blind Navigation with a Wearable Range Camera and Vibrotactile Helmet", Proceedings of the ACM Multimedia, Nov. 28, 2011, 4 pages.

Ran, Lisa et al., "Drishti: An Integrated Indoor/Outdoor Blind Navigation System and Service" Proceedings of the Second IEEE Annual Conference on Pervasive Computing and Communications, Mar. 14, 2004, 8 pages.

Nokia, "Nokia User's Guides Terms and Conditions", Jun. 1998, 96 pages (See NPL 2, International Search Report issued in Application No. PCT/US2015/012329 for Explanation of Relevance).

ISA European Patent Office, International Search Report and Written Opinion issued in Patent Application No. PCT/US2015/012329, May 29, 2015, Netherlands, 14 Pages.

\* cited by examiner

AUDIO NAVIGATION ASSISTANCE

BACKGROUND

Persons with physiological visual impairments may utilize one or more mobility aids to navigate their surroundings. Such mobility aids may include, for example, canes, assistance animals, vision enhancement devices, and the like. Similarly, sighted persons encountering situational visual impairment, such as a dark or smoke-filled room, may also benefit from mobility aids that provide navigation assistance for their current environment.

Some mobility aids provide tactile feedback that indicates aspects of the user's surroundings, such as a cane contacting a curb on a street. However, using such aids may occupy a significant amount of the user's attention along with a hand of the user. Additionally, such aids generally provide the same amount and type of feedback of the user's immediate surroundings regardless of the context of those surroundings. As such, these aids are generally incapable of modifying or enhancing the utility of their feedback based on the context of the user's current environment.

SUMMARY

Various embodiments are disclosed herein that relate to providing navigation assistance in an environment via audio output. For example, one disclosed embodiment provides, in a head-mounted computing device, a method comprising receiving depth image data and visible image data from the environment. Using the depth image data and visible image data, a three-dimensional mesh of at least a portion of the environment is generated. Using the three-dimensional mesh, at least one feature in the environment is detected. When the head-mounted computing device is operating in a familiar navigation mode, and based on detecting the feature, a first audio navigation cue of the environment is outputted to the user via one or more transducers. When the head-mounted computing device is operating in the unfamiliar navigation mode, and based on detecting the feature, a second audio navigation cue of the environment is outputted to the user via the one or more transducers, where the second audio navigation cue differs from the first audio navigation cue.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

Figure 1:
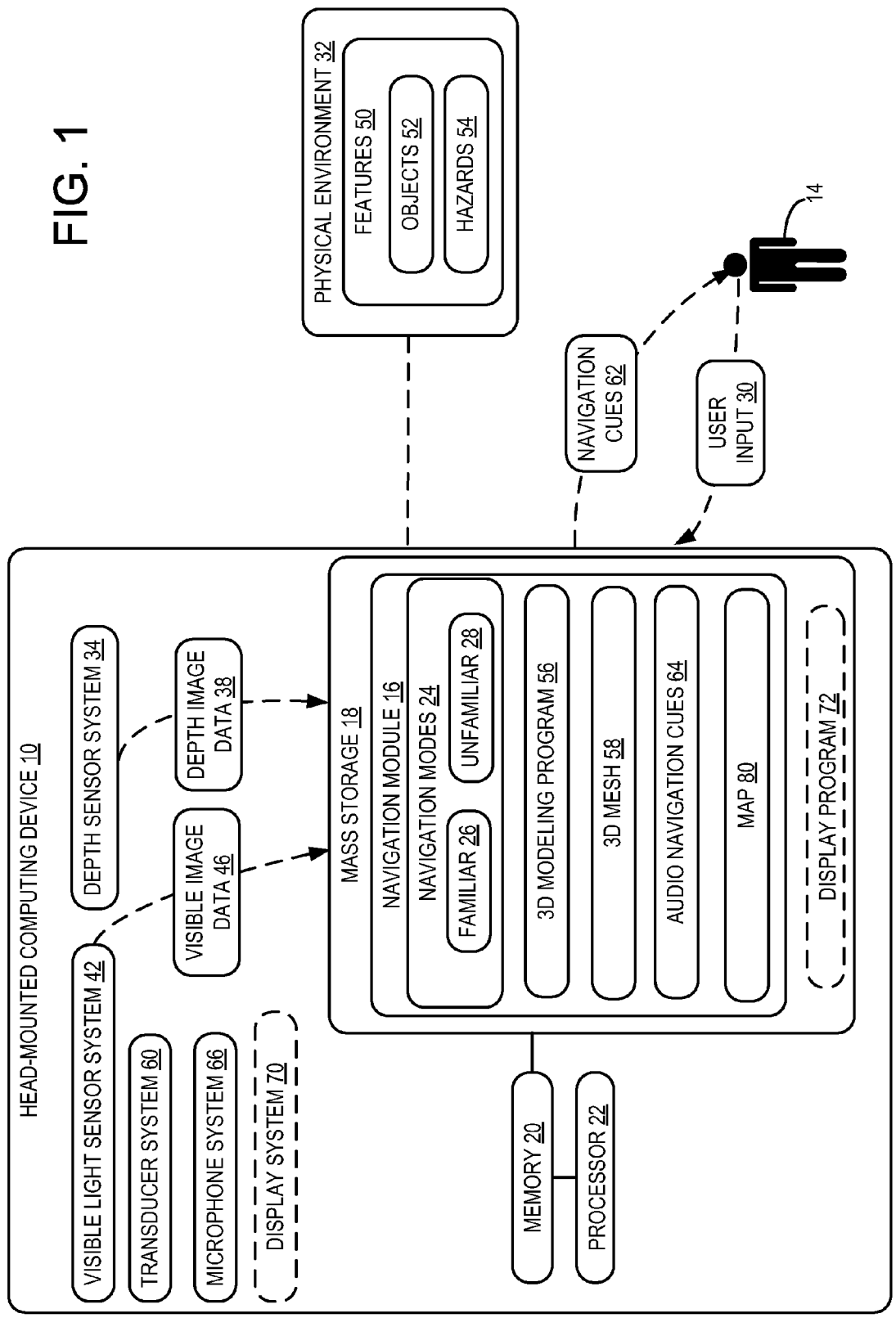
FIG. 1 is a schematic view of a head-mounted computing device for providing navigation assistance according to an embodiment of the present disclosure.

FIG. 1 shows a schematic view of one embodiment of head-mounted computing device 10 for providing navigation assistance to a user 14. The head-mounted computing device 10 includes a navigation module 16 that may be stored in mass storage 18 of the head-mounted computing device 10. The navigation module 16 may be loaded into memory 20 and executed by a processor 22 of the head-mounted computing device 10 to perform one or more of the methods and processes described in more detail below.

The navigation module 16 includes a plurality of navigation modes 24 comprising a familiar navigation mode 26 and an unfamiliar navigation mode 28. Advantageously and described in more detail below, one or more of the navigation modes 24 may be selectively engaged to provide navigation assistance that is tailored to a user's particular needs in a context-appropriate manner. For example, the familiar navigation mode 26 may be engaged, programmatically or via user input 30, when the user 14 is navigating an environment that is familiar to the user. In the familiar navigation mode 26, navigation assistance may be tailored to account for the user's familiarity with her surroundings.

In a similar manner, the unfamiliar navigation mode 28 may be engaged, programmatically or via user input 30, when the user 14 is navigating an environment that is unfamiliar to the user. In the unfamiliar navigation mode 28, navigation assistance may be tailored to account for the user's unfamiliarity with her surroundings. It will be appreciated that the navigation module 16 may also include one or more additional navigation modes 24 that relate to environments or surroundings having particular characteristics or aspects such as, for example, an indoor navigation mode, outdoor navigation mode, urban navigation mode, rural navigation mode, etc. In some examples, two or more navigation modes may be engaged simultaneously, such as for example a familiar navigation mode and an indoor navigation mode.

Figure 2:
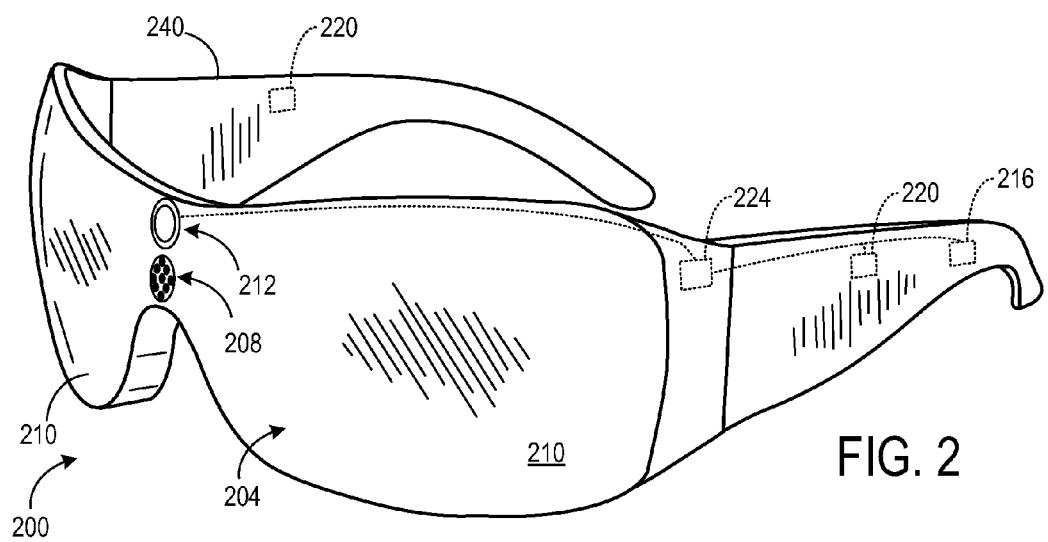
FIG. 2 shows an example head-mounted computing device according to an embodiment of the present disclosure.

The head-mounted computing device 10 may include various sensors and related systems that receive physical environment data from a physical environment 32. With reference now also to FIG. 2, one example of a head-mounted computing device 200 in the form of a pair of wearable glasses is provided. In some examples, the head-mounted computing device 200 may comprise a transparent, semi-transparent or non-transparent display 204 that is supported in front of a viewer's eye or eyes. In other examples, the head-mounted computing device 200 may take a variety of other forms that may or may not comprise a display that is supported in front of a user's eye or eyes.

For example, in some embodiments the head-mounted computing device 10 may comprise a pair of eyeglass frames that do not include a display. Accordingly, many other types and configurations of head-mounted computing devices 10 having various form factors may also be used and are within the scope of the present disclosure. It will also be appreciated that the head-mounted computing device 10 shown in FIG. 1 may take the form of the head-mounted computing device 200 shown in FIG. 2, as described in more detail below, or any other suitable head-mounted computing device.

With reference to FIGS. 1 and 2, in this example the head-mounted computing device 10 includes a depth sensor system 34 that includes one or more depth cameras 208 that generate depth image data 38. Depth sensor system 34 may also detect movements within its field of view, such as gesture-based inputs or other movements performed by user 14 or by a person or physical object within the user's field of view. In one example, each depth camera 208 may include left and right cameras of a stereoscopic vision system. Time-resolved images from one or more of these depth cameras may be registered to each other and/or to images from another optical sensor such as a visible spectrum camera, and may be combined to yield depth-resolved video.

In other examples, a structured light depth camera may be configured to project a structured infrared illumination, and to image the illumination reflected from a scene onto which the illumination is projected. A depth map of the scene may be constructed based on spacings between adjacent features in the various regions of an imaged scene. In still other examples, a depth camera may take the form of a time-of-flight depth camera configured to project a pulsed infrared illumination onto a scene and detect the illumination reflected from the scene. It will be appreciated that any other suitable depth camera may be used within the scope of the present disclosure.

The head-mounted computing device 10 may also include a visible light sensor system 42 that utilizes at least one outward facing sensor 212, such as an RGB camera or other optical sensor. The visible light sensor system 42 may generate visible image data 46 that is provided to the navigation module 16. Outward facing sensor 212 may capture two-dimensional image information from physical environment 32 and features 50 within the environment. As described in more detail below, features 50 may include physical objects 52 and hazards 54 in the environment 32. In some examples, a physical object 52 may also comprise a hazard 54. Outward facing sensor 212 may capture images of the physical environment 32 in which user 14 is situated.

The head-mounted computing device 10 may also include a 3D modeling program 56 that uses depth image data 38 and visible image data 46 to generate a three-dimensional mesh 58 that models at least a portion of the physical environment 32 surrounding the user 14. In some examples, the 3D modeling program 56 may utilize polygonal modeling techniques in which vertices in 3D space are connected by line segments to form a textured, 3D polygonal mesh. It will also be appreciated that other techniques for 3D modeling may be utilized including, but not limited to, curve modeling and digital sculpting techniques.

The head-mounted computing device 10 may also include a transducer system 60 comprising one or more actuators that convert an electrical signal from the navigation module 16 into another form of energy. As described in more detail below, the navigation module 16 may utilize the transducer system 60 to output navigation cues 62 of the environment 32 to the user 14. With reference again to FIG. 2 and in some examples, the transducer system 60 may include one or more speakers 216 for generating audio navigation cues 64. In other examples, the one or more speakers 216 may take the form of headphones or in-ear ear buds worn by the user 14.

In some examples, the navigation module 16 and/or transducer system 60 may process the audio navigation cues 64 to enable the user 14 to perceive that the cues originate at a particular location in 3D space of the physical environment 32. For example, one or more crosstalk cancellation mechanisms may be utilized and configured such that a first audio signal (e.g., left channel) is delivered to a first ear (e.g., left ear) and a second audio signal (e.g., right channel) is delivered to a second ear (e.g., right ear) while substantially attenuating the delivery of the first audio signal to the second ear and delivery of the second audio signal to the first ear.

In other examples, the provision of three-dimensional audio may be based on a head-related transfer function "HRTF" and/or head-related impulse response "HRIR" to create the illusion that sound is originating from a particular location in 3D acoustic space. The HRTF describes how a given sound wave input is filtered by the diffraction and reflection properties of the head and pinna before the sound reaches the eardrum and inner ear. In other words, an HRTF may be defined based on the difference between a sound in free air and the sound as it arrives at the eardrum.

In other examples the transducer system 60 may include one or more tactile transducers 220 for generating haptic navigation cues to the user 14, such as vibrations.

The head-mounted computing device 10 may also include a microphone system 66 and one or more microphones 224 for receiving audio input from the physical environment 32. In some examples, a microphone array that includes a plurality of microphones 224 positioned at various locations on the head-mounted computing device 200 may be provided. The microphones 224 may comprise omnidirectional microphones and/or unidirectional microphones that are configured to receive speech and other audio inputs from the physical environment 32.

In some examples, the microphone system 66 and/or navigation module 16 may utilize one or more acoustic source localization techniques to locate audio sources in the 3D space of the physical environment 32, including sources located behind the user 14. For example, the microphone system 66 and/or navigation module 16 may apply one or more beamforming techniques to at least a portion of the audio inputs from the microphone array. For example, a single, directionally-adaptive sound signal may be determined in any suitable manner. The directionally-adaptive sound signal may be determined based on a time-invariant beamforming technique, adaptive beamforming technique, or a combination of time-invariant and adaptive beamforming techniques. The resulting combined signal may have a narrow directivity pattern, which may be steered in a direction of an audio source. It will also be appreciated that any suitable acoustic source localization technique may be used to identify the location of an audio source.

As noted above, in some examples the head mounted computing device 200 may include a display system 70 and display 204 that enables visual navigation cues to be delivered to the eyes of a user 14. In one example, the display 204 may comprise a transparent display configured to visually augment an appearance of the physical environment 32 to user 14 viewing the environment through the transparent display. For example, the appearance of the physical environment 32 may be augmented by graphical content (e.g., one or more pixels each having a respective color and brightness) that is presented via the transparent display to create a mixed reality environment.

In this example the transparent display 204 may also be configured to enable a user to view a physical, real-world object 52 in the physical environment 32 through one or more partially transparent pixels that are displaying a virtual object representation. In one example, the transparent display 204 may include image-producing elements located within lenses 210 (such as, for example, a see-through Organic Light-Emitting Diode (OLED) display). As another example, the transparent display 204 may include a light modulator on an edge of the lenses 210. In this example the lenses 210 may serve as a light guide for delivering light from the light modulator to the eyes of a user. Such a light guide may enable a user to perceive a 2D image or a 3D holographic image located within the physical environment 32 that the user is viewing, while also allowing the user to view physical objects 52 in the physical environment.

With reference again to the head-mounted computing device 10 of FIG. 1, it will be appreciated that the processor 22 may comprise a logic subsystem and the memory 20 may comprise a storage subsystem, as discussed in more detail below with respect to FIG. 9, that are in communication with the various sensors and corresponding systems described above. In one example, the storage subsystem may include instructions that are executable by the logic subsystem to receive signal inputs from the sensors and forward such inputs (in unprocessed or processed form) to the navigation module 16.

Additionally, the example illustrated in FIG. 1 shows the mass storage 18, memory 20 and processor 22 integrated into the head-mounted computing device 10. It will be appreciated that in other examples one or more of the mass storage 18, memory 20 and processor 22 may be located in one or more other computing devices to which the head-mounted computing device 10 is communicatively coupled. For example, the head-mounted computing device 10 may be operatively connected with another computing device using a wired connection, or may employ a wireless connection via WiFi, Bluetooth, or any other suitable wireless communication protocol. Additional details regarding the components and computing aspects of the head-mounted computing device 10 and other computing device(s) are described in more detail below with reference to FIG. 9.

It will be appreciated that the head-mounted computing device 10 and related sensors and other components described above and illustrated in FIGS. 1 and 2 are provided by way of example. These examples are not intended to be limiting in any manner, as any other suitable sensors, components, and/or combination of sensors and components may be utilized. Therefore it is to be understood that the head-mounted computing device 10 may include additional and/or alternative sensors, cameras, microphones, input devices, output devices, etc. without departing from the scope of this disclosure. Further, the physical configuration of the head-mounted computing device 10 and its various sensors and subcomponents may take a variety of different forms without departing from the scope of this disclosure.

Figure 3:
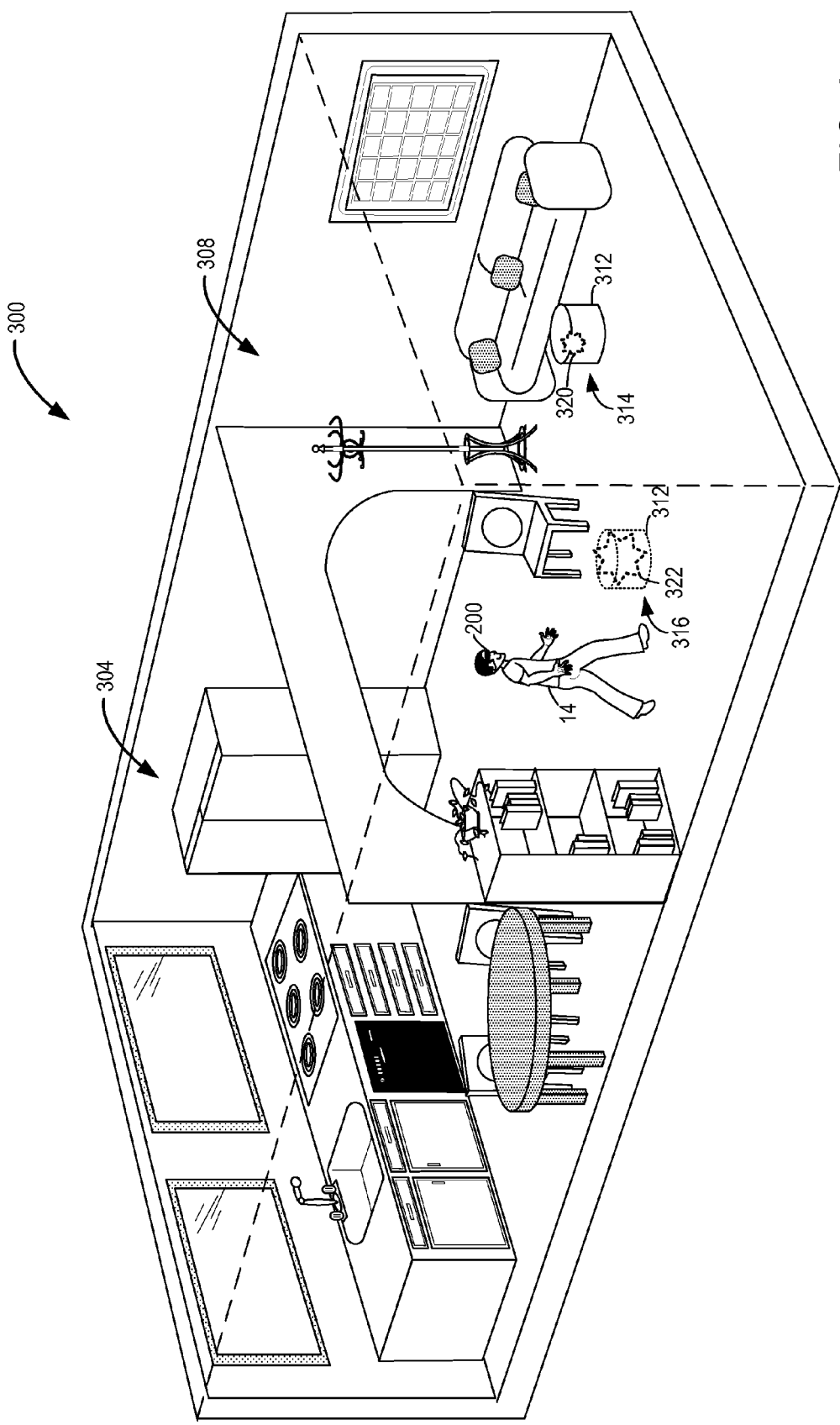
FIG. 3 is a schematic illustration of a user wearing the head-mounted computing device of FIG. 2 in a home.
Figure 4:
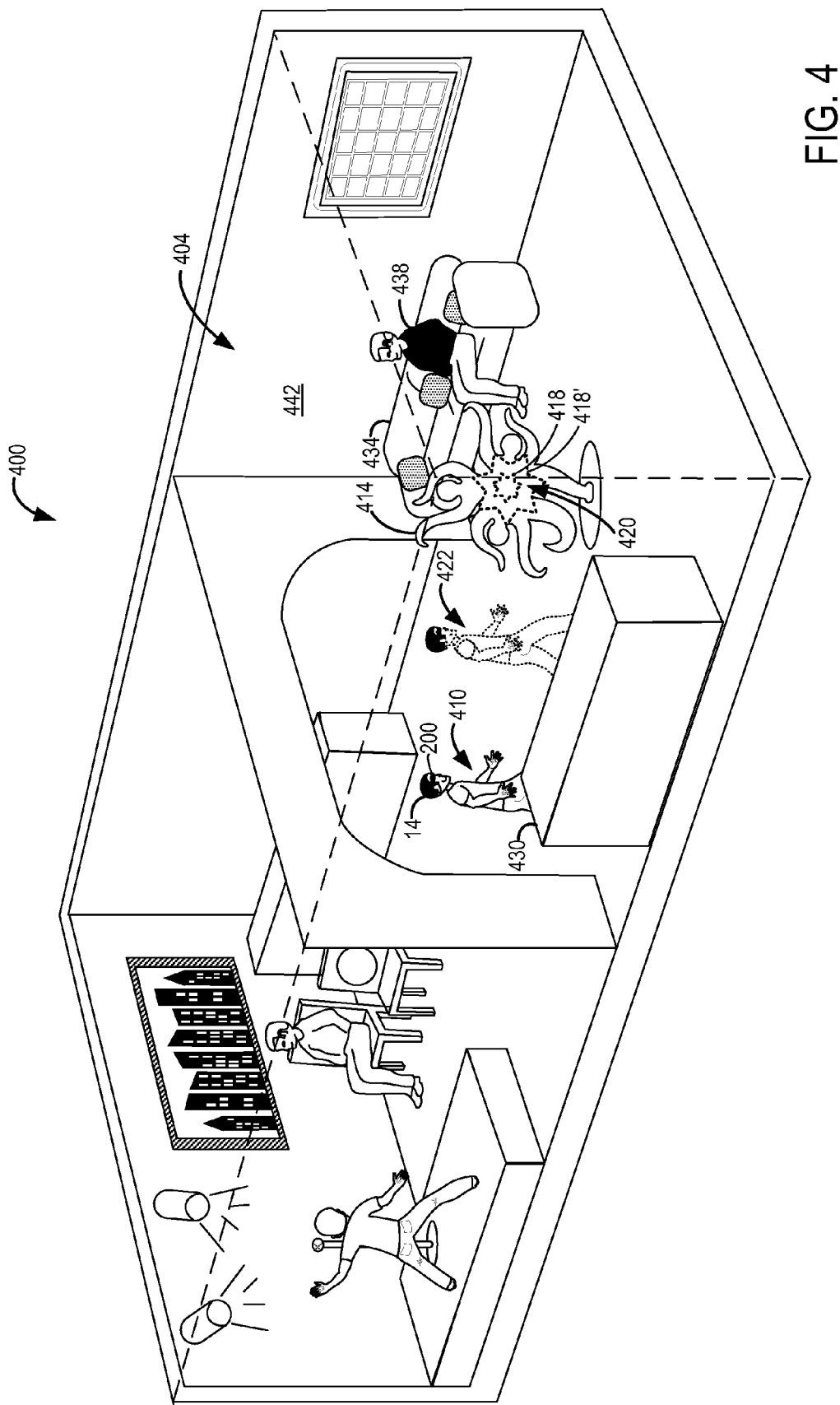
FIG. 4 is a schematic view of the user of FIG. 3 wearing the head-mounted computing device in a hotel.

With reference now to FIGS. 3-7, descriptions of example use cases and embodiments of the head-mounted computing device 10 will now be provided. In FIG. 3 a user 14 wearing the head-mounted computing device 200 of FIG. 2 may be walking in his home 300. The user 14 may have a vision impairment and may use the head-mounted computing device 200 for navigation assistance. In one example, the user 14 may initialize the head-mounted computing device 200 by walking from room to room in his home 300 and, for each room, providing user input 30 of a room identifier that identifies the room.

For example, while the user 14 walks around the kitchen 304, the user may say, "This is my kitchen". The navigation module 16 may receive this user input 30, process it using a voice recognition program and tag the kitchen 304 with a "Kitchen" identifier. The navigation module 16 may use the visible image data 46 and depth image data 38 of the kitchen 304 to generate a 3D mesh of the kitchen and its various features 50, such as appliances, furniture, walls, contours, surfaces, etc. The navigation module 16 may also generate a corresponding map 80 of the home 300 that includes the kitchen 304 tagged with the "Kitchen" identifier. In a similar manner, the navigation module 16 may use visible image data 46 and depth image data 38 of the living room 308 to generate a 3D mesh of this room and its various features 50. The navigation module may tag the living room with a "Living Room" identifier based on user input 30 from the user 14, and may add the living room 308 tagged with the "Living Room" identifier to the map 80 of the home 300. As the user 14 walks from room to room and around the home 300, the navigation module 16 may also recognize and store common pathways the user takes when navigating the house.

Subsequently, when the user 14 enters one of these rooms, the navigation module 16 may identify the room via the map 80 and detect the room as tagged with the corresponding room identifier. Accordingly and based at least on detecting the room as tagged with the corresponding room identifier, the navigation module 16 may engage the familiar navigation mode 26. In other examples, a room or other portion of a physical environment 32 may not be associated with an identifier, but may have been previously visited by the user 14. In these examples, the navigation module 16 may recognize the room or other portion of the environment 32 from the user's one or more previous visits by utilizing, for example, machine learning techniques. If the user has visited the room or other portion of the environment 32 at least a predetermined number of times, such as 1, 3, 5 or any other suitable number, then the navigation module 16 may engage the familiar navigation mode 26. In still other examples, the user 14 may provide user input 30 to the navigation module 16 that engages the familiar navigation mode 26.

With continued reference to FIG. 3 and as described in more detail below, while in the familiar navigation mode 26 the navigation module 16 may provide navigation cues 62 to the user 14 that are different from the navigation cues provided when the navigation module 16 is operating in the unfamiliar navigation mode 28. In one example, the user 14 may be walking in the general direction of the ottoman 312 located at a usual location 314. In the familiar navigation mode 26, the navigation module 16 may not provide a navigation cue 62 corresponding to the ottoman 312, under the assumption that the user 14 remembers the usual location 314 of the ottoman 312 from previous visits to the living room 308. In another example, the navigation module 16 may output an audio navigation cue 64 that comprises a gentle reminder of the ottoman 312, such as vocalizing "Ottomon" in a soft voice via speaker 216.

In another example, the user 14 may be a first-time guest in the home 300. Accordingly the navigation module 16 may engage the unfamiliar navigation mode 28. In this mode, as the user 14 walks in the general direction of the ottoman 312, the navigation module 16 may provide an audio navigation cue 64 to the user that alerts the user to the location of the ottoman. For example, the navigation module 16 may output a brief, distinctive sound (or earcon), illustrated as familiar earcon 320, using one or more acoustic source localization techniques that cause the user 14 to perceive the earcon as originating at the usual, 3D location 314 corresponding to the ottoman 312. In another example, the navigation module 16 may vocalize the word "Ottoman" to the user 14 from the usual location 314 using an acoustic source localization technique.

In another example and while in the familiar navigation mode 26, the navigation module 16 may recognize that the ottoman 312 is in an unusual location 316 that is different from its usual location 314. Further and also based on the user's direction of movement, the navigation module 16 may determine that in unusual location 316 the ottoman 312 is in the direct path of the user 14. The navigation module 16 may determine that in this situation the ottoman 312 poses a tripping hazard to the user 14.

Accordingly, the navigation module 16 may classify the ottoman 312 as a hazard 54 and may output an audio navigation cue 64 in the form of an alert earcon 322 utilizing an acoustic source localization technique that warns the user of the unusual location 316 of the ottoman 312. In this example, the ottoman 312 may be classified as both an object 52 and a hazard 54 by the navigation module 16. Additionally and to convey a sense of urgency to the user 14, the alert earcon 322 may be outputted with a higher volume as compared to the familiar earcon 320, as depicted in FIG. 3 by the alert earcon 322 having a larger size than the familiar earcon 320. In other examples, the alert earcon 322 may comprise a different distinctive sound or sounds as compared to the familiar earcon 320.

In some examples, the navigational module 16 may output audio navigation cues 64 for a feature 50 in the environment 32 at increasing volumes as the proximity of the feature to the user 14 decreases. For example and with reference now to FIG. 4, the user 14 may be in the lobby 404 of a hotel 400 for the first time. Accordingly, the navigation module 16 may be operating in the unfamiliar navigation mode 28. The user 14 may be at an initial position 410 that is a first distance away from the sculpture 414, and may be walking towards the sculpture in the center of the lobby 404. When the user 14 is at the initial position 410, the navigation module 16 may output a sculpture earcon 418 at a first volume that causes the user 14 to perceive the sculpture earcon as originating at the 3D location 420 corresponding to the sculpture. As the user 14 continues walking toward the sculpture 414 and reaches a subsequent position 422, the navigation module 16 may output the sculpture earcon at a second volume greater than the first volume, as indicated by the larger sculpture earcon 418', to alert the user that he is closer to the sculpture 414.

In some examples in the unfamiliar navigation mode 28, the navigation module 16 may output an audio navigation cue 64 corresponding to each feature 50 in the physical environment 32 in which the user 14 is located. For example, in FIG. 4 the navigation module 16 may output an audio navigation cue 64 corresponding to each feature that is within the field of view of the user 14. When the user 14 is at the initial position 410, the navigation module 16 may output an audio navigation cue 64 corresponding to the sculpture 414, desk 430, couch 434, person 438 and wall 442.

In another example, the navigation module 16 may use one or more of the depth image data 38 and visible image data 46 to recognize the face of the person 438 sitting on the couch 434. The navigation module may then associate the person's face with an identity of the person, using for example a facial recognition database stored in a remote server. The navigation module may then inform the user 14 of the identity of the person 438. Advantageously, the user 14 may thereby anticipate a person who is in the vicinity of the user.

Further and in some examples, an identity earcon may be assigned to the identity of the person 438, with the identity earcon being provided to the navigation module 16 via user input 30 or being programmatically generated by the navigation module. In these examples, when the navigation module 16 associates the face with the identity of the person 438, the navigation module 16 may output the identity earcon to the user to inform the user of the identity of the person.

Figure 5:
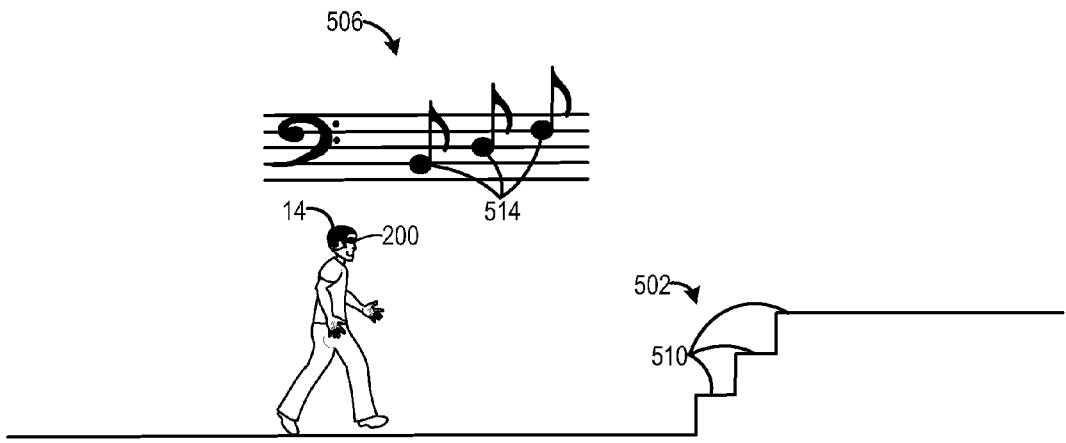
FIG. 5 is a schematic view of a user wearing the head-mounted computing device of FIG. 2 approaching a slope comprising stairs.

With reference now to FIG. 5, in another example an audio navigation cue 64 may be customized to identify a slope in the physical environment 32. In one example the user 14 may be approaching an inclined slope 502. The navigation module 16 may recognize the inclined slope 502 and may correspondingly output to the user 14 an audio navigation cue 64 comprising a plurality of ascending pitched sounds 506 that indicate an inclined slope.

Figure 6:
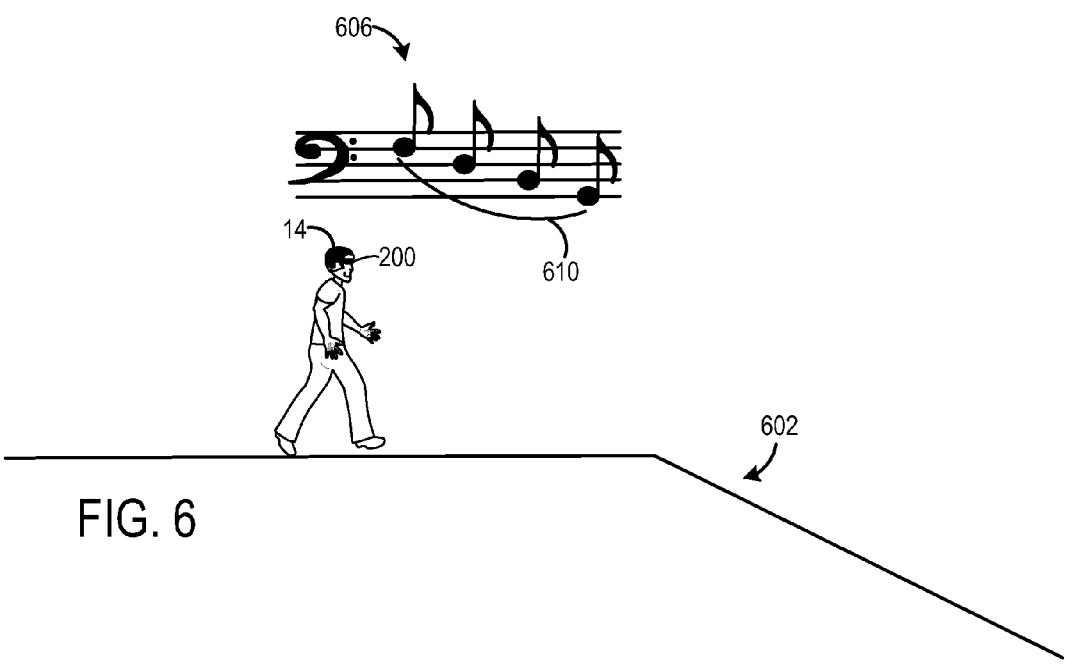
FIG. 6 is a schematic view of the user of FIG. 6 approaching a continuous declined slope.

In another example and with reference now to FIG. 6, the user 14 may be approaching a declined slope 602. The navigation module 16 may recognize the declined slope 602 and may correspondingly output to the user 14 an audio navigation cue 64 comprising a plurality of descending pitched sounds 606 that indicate a declined slope.

With reference again to FIG. 5, in some examples the navigation module 16 may recognize the inclined slope 502 as one or more steps 510, such as in a flight of stairs. In response, the navigation module 16 may correspondingly output to the user 14 an audio navigation cue 64 comprising a plurality of discrete ascending pitched sounds 506, as indicated by the individual eighth notes 514. In this manner, the navigation module 16 may communicate to the user 14 that ascending steps are ahead. In a similar manner, where the navigation module 16 recognizes a declined slope as one or more steps, the navigation module 16 may correspondingly output to the user 14 an audio navigation cue 64 comprising a plurality of discrete descending pitched sounds. In this manner, the navigation module 16 may communicate to the user 14 that descending steps are ahead.

In some examples, the navigation module may identify the number of steps in an inclined or declined slope, and may communicate the number of steps to the user 14 via a number of discrete pitched sounds that correspond to the number of steps. For example and as shown in FIG. 5, the navigation module 16 may recognize three steps 510 in the inclined slope 502. Accordingly, the navigation module 16 may output to the user 14 three discrete pitched sounds in the form of three eighth notes 514. Advantageously, in this manner the user 14 may be conveniently informed that three ascending steps are ahead.

With reference again to FIG. 6, in some examples the navigation module 16 may recognize the declined slope 602 as comprising a continuous slope in the form of a declined grade, such as an downwardly sloped sidewalk, street, hallway, etc., that may be substantially planar as shown in FIG. 6, or may be undulating or somewhat rolling. In response, the navigation module 16 may correspondingly output to the user 14 an audio navigation cue 64 comprising a plurality of continuous descending pitched sounds 606, as indicated by the slur 610 connecting the four eighth notes in FIG. 6.

In some examples, the audio navigation cue 64 outputted to the user 14 to identify a slope may be different in the familiar navigation mode 26 as compared to the unfamiliar navigation mode 28. For example and with reference again to FIG. 5, the discrete ascending pitched sounds 506 indicating steps 510 may be outputted at a first, lower volume when the navigation module 16 is operating in the familiar navigation mode 26 (such as, for example, when the user 14 is in his home). However when the navigation module 16 is operating in the unfamiliar navigation mode 28 (such as, for example, when the user 14 is in a building for the first time), the discrete ascending pitched sounds 506 indicating steps 510 may be outputted at a second, higher volume to provide greater notice to the user of the stairs.

In some examples and as noted above, the navigation module 16 may be configured to output a haptic navigation cue to the user 14 via one or more tactile transducers 220. For example and with reference also to FIG. 4, the head-mounted computing device 200 worn by user 14 may include a tactile transducer 220 on the right temple arm 240 of the device, where the tactile transducer is configured to generate vibrations that are felt by the user 14. When the user 14 is at initial position 410, and to alert the user of the desk 430 to the immediate right of the user, the navigation module 16 may cause the tactile transducer 220 on the right temple arm 240 of the head-mounted computing device 200 to vibrate in a predetermined pattern that indicates an object is nearby and to the right of the user 14.

Figure 7:
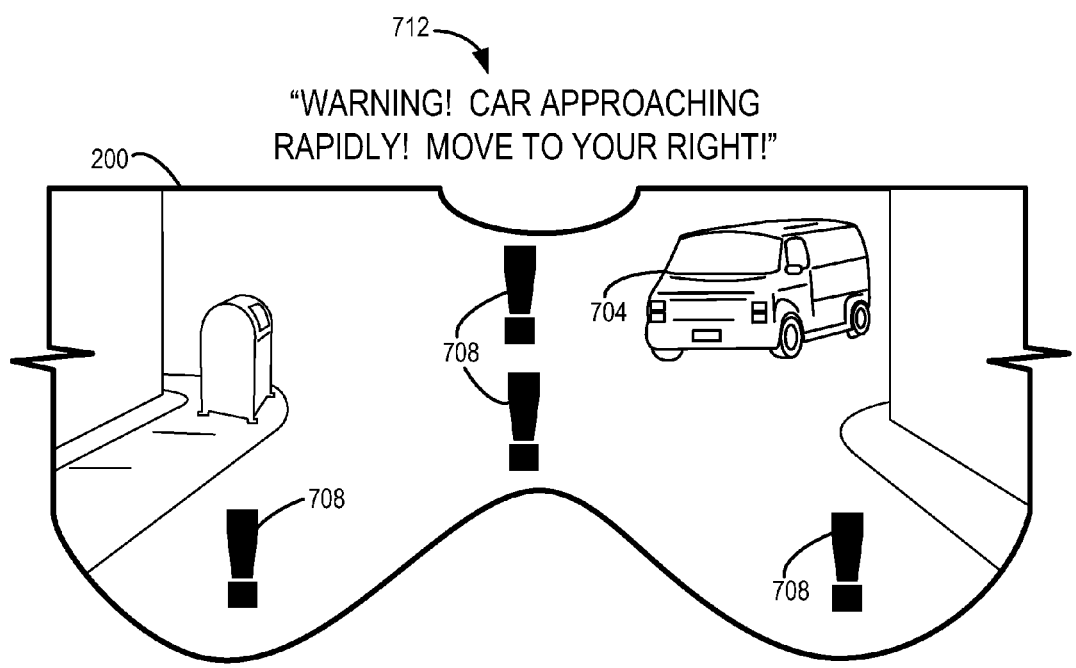
FIG. 7 is a schematic view of an outdoor environment as viewed via a head-mounted computing device according to an embodiment of the present disclosure.

With reference now to FIG. 7, in some examples the navigation module 16 may also be configured to display a visual navigation cue to the user 14 via a display system 70 of a head-mounted computing device 10. In one example, the user 14 may have a sight impairment comprising significant myopia that limits the user's ability to see distant objects. The user 14 may be walking down a city street, with the view of the street through a transparent display 204 of the head-mounted computing device 200 shown in FIG. 7. A van 704 may be driving toward the user 14.

The navigation module 16 may use depth image data 38 to determine three-dimensional locations of the van 704 as it moves toward the user 14, and may determine that the van is on a path that may hit the user 14. Accordingly, the navigation module 16 may display multiple, flashing warning icons 708 on the transparent display 204 to alert the user to the approaching hazard. In some examples, the navigation module 16 may also output an audio navigation cue 64 alerting the user to the approaching hazard. For example, the audio navigation cue 64 may comprise one or more vocalized warnings and related instructions 712, such as "Warning! Car approaching rapidly! Move to your right!"

As noted above, in some examples the head-mounted computing device 10 may include a display system 70. Where the head-mounted computing device 10 includes a display system 70, in some examples the head-mounted computing device 10 may output audio navigation cues 64 as described above while not displaying images or other visual content to the user via the display system 70.

Figure 8A:
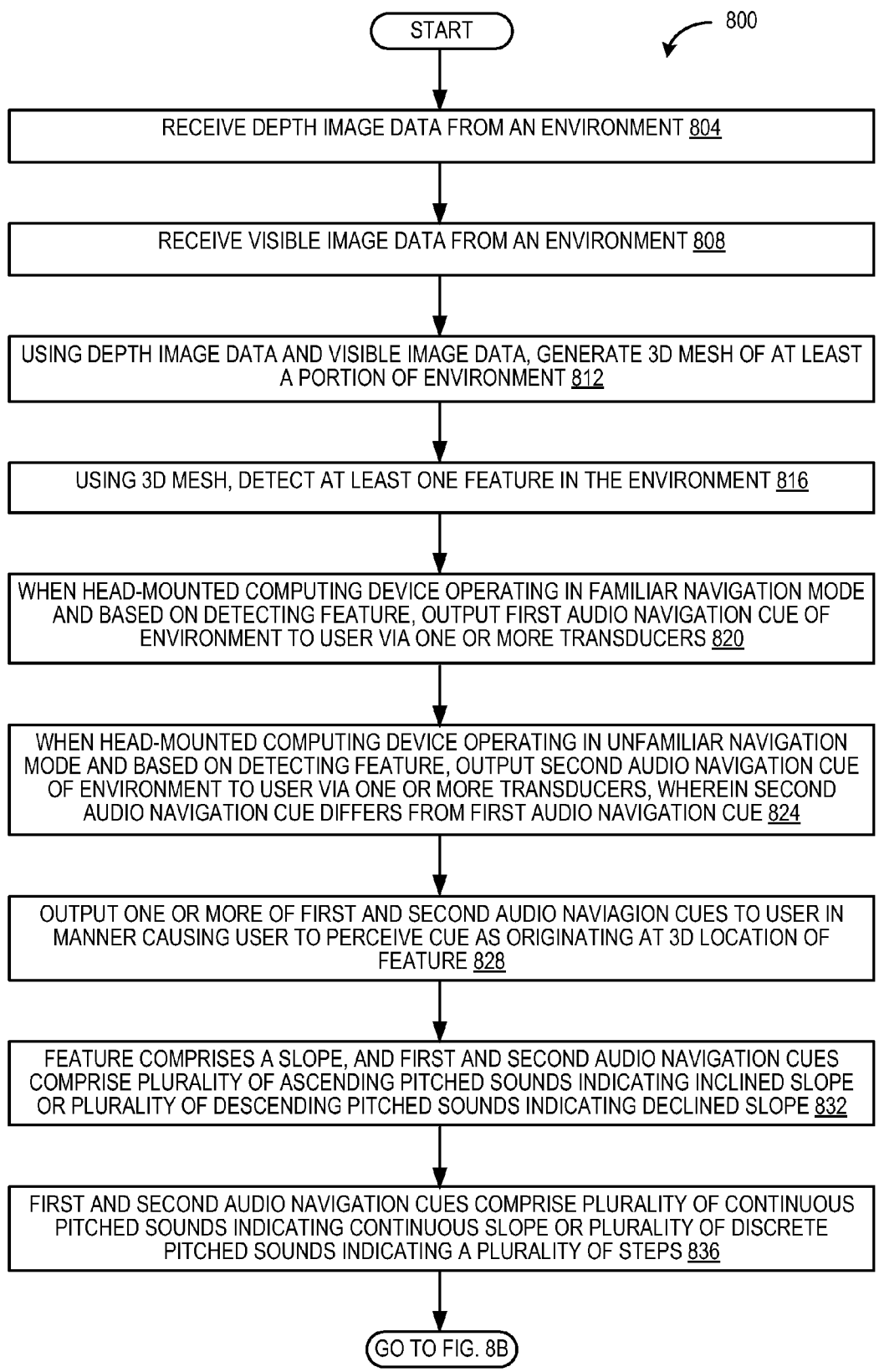
FIGS. 8A and 8B are a flow chart of a method for providing navigation assistance to a user in an environment via audio output according to an embodiment of the present disclosure.
Figure 8B:
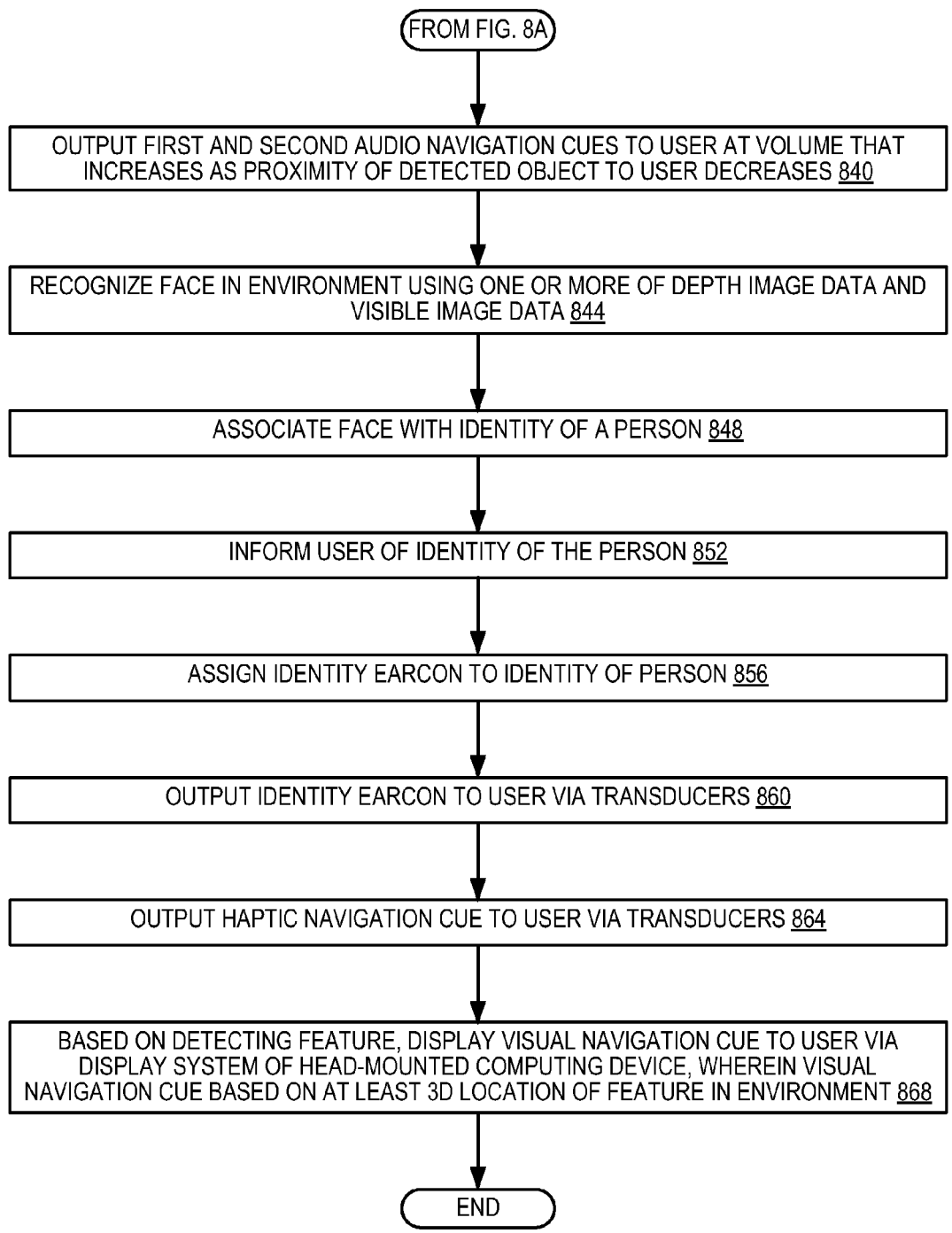

FIGS. 8A and 8B illustrate a flow chart of a method 800 for providing navigation assistance to a user in an environment via audio output according to an embodiment of the present disclosure. The following description of method 800 is provided with reference to the software and hardware components of the head-mounted computing device 10 described above and shown in FIGS. 1-7. It will be appreciated that method 800 may also be performed in other contexts using other suitable hardware and software components.

With reference to FIG. 8A, at 804 the method 800 may include receiving depth image data from the environment. At 808 the method 800 may include receiving visible image data from the environment. At 812 the method 800 may include, using the depth image data and visible image data, generating a three-dimensional mesh of at least a portion of the environment. At 816 the method 800 may include, using the three-dimensional mesh, detecting at least one feature in the environment. At 820 the method 800 may include, when the head-mounted computing device is operating in a familiar navigation mode and based on detecting the feature, outputting a first audio navigation cue of the environment to the user via the one or more transducers.

At 824 the method 800 may include, when the head-mounted computing device is operating in an unfamiliar navigation mode and based on detecting the feature, outputting a second audio navigation cue of the environment to the user via the one or more transducers, wherein the second audio navigation cue differs from the first audio navigation cue. At 828 the method 800 may include outputting one or more of the first audio navigation cue and the second audio navigation cue to the user in a manner that causes the user to perceive the cue as originating at a three-dimensional location of the feature. At 832 the feature may comprise a slope, and the first audio navigation cue and the second audio navigation cue comprise a plurality of ascending pitched sounds that indicate an inclined slope or a plurality of descending pitched sounds that indicate a declined slope.

At 836 the first audio navigation cue and the second audio navigation cue may comprise a plurality of continuous pitched sounds that indicate a continuous slope or a plurality of discrete pitched sounds that indicate a plurality of steps. With reference now to FIG. 8B, at 840 the method 800 may include outputting the first audio navigation cue and the second audio navigation cue to the user at a volume that increases as a proximity of the detected object to the user decreases. At 844 the method 800 may include recognizing a face in the environment using one or more of the depth image data and the visible image data. At 848 the method 800 may include associating the face with an identity of a person. At 852 the method 800 may include informing the user of the identity of the person.

At 856 the method 800 may include assigning an identity earcon to the identity of the person. At 860 the method 800 may include outputting the identity earcon to the user via the one or more transducers. At 864 the method 800 may include outputting a haptic navigation cue to the user via the one or more transducers. At 868 the method 800 may include, based on detecting the feature, displaying a visual navigation cue to the user via a display system of the head-mounted computing device, wherein the visual navigation cue is based on at least a three-dimensional location of feature in the environment.

It will be appreciated that method 800 is provided by way of example and is not meant to be limiting. Therefore, it is to be understood that method 800 may include additional and/or alternative steps than those illustrated in FIGS. 8A and 8B. Further, it is to be understood that method 800 may be performed in any suitable order. Further still, it is to be understood that one or more steps may be omitted from method 800 without departing from the scope of this disclosure.

Figure 9:
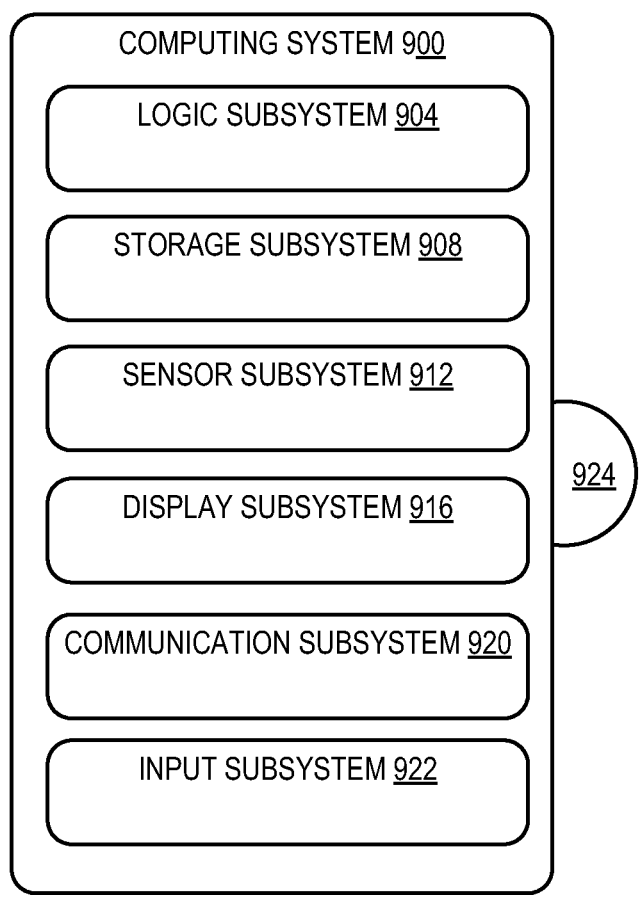
FIG. 9 is a simplified schematic illustration of an embodiment of a computing device.

FIG. 9 schematically shows a nonlimiting embodiment of a computing system 900 that may perform one or more of the above described methods and processes. Head-mounted computing device 10 may take the form of or include one or more aspects of computing system 900. Computing system 900 is shown in simplified form. It is to be understood that virtually any computer architecture may be used without departing from the scope of this disclosure. In different embodiments, computing system 900 may take the form of a mainframe computer, server computer, desktop computer, laptop computer, tablet computer, home entertainment computer, network computing device, mobile computing device, mobile communication device, gaming device, etc.

As shown in FIG. 9, computing system 900 includes a logic subsystem 904, storage subsystem 908, and sensor subsystem 912. Computing system 900 may optionally include a display subsystem 916, communication subsystem 920, input subsystem 922 and/or other subsystems and components not shown in FIG. 9. Computing system 900 may also include computer readable media, with the computer readable media including computer readable storage media and computer readable communication media. Computing system 900 may also optionally include other user input devices such as keyboards, mice, game controllers, and/or touch screens, for example. Further, in some embodiments the methods and processes described herein may be implemented as a computer application, computer service, computer API, computer library, and/or other computer program product in a computing system that includes one or more computers.

Logic subsystem 904 may include one or more physical devices configured to execute one or more instructions. For example, the logic subsystem 904 may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

The logic subsystem 904 may include one or more processors that are configured to execute software instructions. Additionally or alternatively, the logic subsystem may include one or more hardware or firmware logic machines configured to execute hardware or firmware instructions. Processors of the logic subsystem may be single core or multi-core, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration.

Storage subsystem 908 may include one or more physical, persistent devices configured to hold data and/or instructions executable by the logic subsystem 904 to implement the herein described methods and processes. When such methods and processes are implemented, the state of storage subsystem 908 may be transformed (e.g., to hold different data).

Storage subsystem 908 may include removable media and/or built-in devices. Storage subsystem 908 may include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Storage subsystem 908 may include devices with one or more of the following characteristics: volatile, nonvolatile, dynamic, static, read/write, read-only, random access, sequential access, location addressable, file addressable, and content addressable.

In some embodiments, aspects of logic subsystem 904 and storage subsystem 908 may be integrated into one or more common devices through which the functionally described herein may be enacted, at least in part. Such hardware-logic components may include field-programmable gate arrays (FPGAs), program- and application-specific integrated circuits (PASIC/ASICs), program- and application-specific standard products (PSSP/ASSPs), system-on-a-chip (SOC) systems, and complex programmable logic devices (CPLDs), for example.

FIG. 9 also shows an aspect of the storage subsystem 908 in the form of removable computer readable storage media 924, which may be used to store data and/or instructions executable to implement the methods and processes described herein. Removable computer-readable storage media 924 may take the form of CDs, DVDs, HD-DVDs, Blu-Ray Discs, EEPROMs, and/or floppy disks, among others.

It is to be appreciated that storage subsystem 908 includes one or more physical, persistent devices. In contrast, in some embodiments aspects of the instructions described herein may be propagated in a transitory fashion by a pure signal (e.g., an electromagnetic signal, an optical signal, etc.) that is not held by a physical device for at least a finite duration. Furthermore, data and/or other forms of information pertaining to the present disclosure may be propagated by a pure signal via computer-readable communication media.

Sensor subsystem 912 may include one or more sensors configured to sense different physical phenomenon (e.g., visible light, infrared light, sound, acceleration, orientation, position, etc.) as described above. Sensor subsystem 912 may be configured to provide sensor data to logic subsystem 904, for example. As described above, such data may include image information, ambient lighting information, depth information, audio information, position information, motion information, user location information, and/or any other suitable sensor data that may be used to perform the methods and processes described above.

When included, display subsystem 916 may be used to present a visual representation of data held by storage subsystem 908. As the above described methods and processes change the data held by the storage subsystem 908, and thus transform the state of the storage subsystem, the state of the display subsystem 916 may likewise be transformed to visually represent changes in the underlying data. The display subsystem 916 may include one or more display devices utilizing virtually any type of technology. Such display devices may be combined with logic subsystem 904 and/or storage subsystem 908 in a shared enclosure, or such display devices may be peripheral display devices. The display subsystem 916 may include, for example, the optional display system 70 and display program 72 of the head-mounted computing device 10.

When included, communication subsystem 920 may be configured to communicatively couple computing system 900 with one or more networks and/or one or more other computing devices. Communication subsystem 920 may include wired and/or wireless communication devices compatible with one or more different communication protocols. As nonlimiting examples, the communication subsystem 920 may be configured for communication via a wireless telephone network, a wireless local area network, a wired local area network, a wireless wide area network, a wired wide area network, etc. In some embodiments, the communication subsystem may allow computing system 900 to send and/or receive messages to and/or from other devices via a network such as the Internet.

When included, input subsystem 922 may comprise or interface with one or more sensors or user-input devices such as a game controller, gesture input detection device, voice recognizer, inertial measurement unit, keyboard, mouse, or touch screen. In some embodiments, the input subsystem 922 may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

The terms "module" and "program" may be used to describe an aspect of the head-mounted computing device 10 that is implemented to perform one or more particular functions. In some cases, such a module or program may be instantiated via logic subsystem 904 executing instructions held by storage subsystem 908. It is to be understood that different modules and programs may be instantiated from the same application, service, code block, object, library, routine, API, function, etc. Likewise, the same module or program may be instantiated by different applications, services, code blocks, objects, routines, APIs, functions, etc. The terms "module" and "program" are meant to encompass individual or groups of executable files, data files, libraries, drivers, scripts, database records, etc.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A head-mounted computing device for providing navigation assistance in an environment via audio output, the head-mounted computing device comprising:
    one or more depth sensors for generating depth image data from the environment;
    one or more visible light sensors for generating visible image data from the environment;
    one or more transducers; and
    a navigation module executed by a processor of the head-mounted computing device, the navigation module comprising a familiar navigation mode and an unfamiliar navigation mode, the navigation module configured to:
        using the depth image data and visible image data, generate a three-dimensional mesh of at least a portion of the environment;
        using the three-dimensional mesh, detect at least one feature in the environment;
        when operating in the familiar navigation mode and based on detecting the feature, output a first audio navigation cue of the environment to the user via the one or more transducers; and
        when operating in the unfamiliar navigation mode and based on detecting the feature, output a second audio navigation cue of the environment to the user via the one or more transducers, wherein the second audio navigation cue differs from the first audio navigation cue.

2. The head-mounted computing device of claim 1, wherein the navigation module is further configured to output one or more of the first audio navigation cue and the second audio navigation cue to the user in a manner that causes the user to perceive the cue as originating at a three-dimensional location of the feature.

3. The head-mounted computing device of claim 1, wherein the feature comprises a slope, and the first audio navigation cue and the second audio navigation cue comprise a plurality of ascending pitched sounds that indicate an inclined slope or a plurality of descending pitched sounds that indicate a declined slope.

4. The head-mounted computing device of claim 3, wherein the first audio navigation cue and the second audio navigation cue further comprise a plurality of continuous pitched sounds that indicate a continuous slope or a plurality of discrete pitched sounds that indicate a plurality of steps.

5. The head-mounted computing device of claim 1, wherein the navigation module is further configured to output the first audio navigation cue and the second audio navigation cue to the user at a volume that increases as a proximity of the feature to the user decreases.

6. The head-mounted computing device of claim 1, wherein the navigation module is further configured to:
    receive user input of a room identifier that identifies a room in the environment; and
    using the room identifier, generate a map of the environment that includes the room tagged with the room identifier.

7. The head-mounted computing device of claim 6, wherein the navigation module is further configured to:
    subsequently detect the room tagged with the room identifier; and
    based on detecting the room tagged with the room identifier, engage the familiar navigation mode and use the map of the environment to provide the first audio navigation cue to the user.

8. The head-mounted computing device of claim 1, wherein the navigation module is further configured to:
    using one or more of the depth image data and the visible image data, recognize a face in the environment;
    associate the face with an identity of a person; and
    inform the user of the identity of the person.

9. The head-mounted computing device of claim 1, wherein the navigation module is further configured to output a haptic navigation cue to the user via the one or more transducers.

10. The head-mounted computing device of claim 1, further comprising a display system for displaying a visual navigation cue to the user, wherein the visual navigation cue is based on at least a three-dimensional location of the feature in the environment.

11. A method for providing navigation assistance to a user in an environment via audio output in a head-mounted computing device, the method comprising:
    receiving depth image data from the environment;
    receiving visible image data from the environment;
    using the depth image data and visible image data, generating a three-dimensional mesh of at least a portion of the environment;
    using the three-dimensional mesh, detecting at least one feature in the environment;
    when the head-mounted computing device is operating in a familiar navigation mode and based on detecting the feature, outputting a first audio navigation cue of the environment to the user via the one or more transducers; and
    when the head-mounted computing device is operating in the unfamiliar navigation mode and based on detecting the feature, outputting a second audio navigation cue of the environment to the user via the one or more transducers, wherein the second audio navigation cue differs from the first audio navigation cue.

12. The method of claim 11, further comprising outputting one or more of the first audio navigation cue and the second audio navigation cue to the user in a manner that causes the user to perceive the cue as originating at a three-dimensional location of the feature.

13. The method of claim 11, wherein the feature comprises a slope, and the first audio navigation cue and the second audio navigation cue comprise a plurality of ascending pitched sounds that indicate an inclined slope or a plurality of descending pitched sounds that indicate a declined slope.

14. The method of claim 13, wherein the first audio navigation cue and the second audio navigation cue further comprise a plurality of continuous pitched sounds that indicate a continuous slope or a plurality of discrete pitched sounds that indicate a plurality of steps.

15. The method of claim 11, further comprising outputting the first audio navigation cue and the second audio navigation cue to the user at a volume that increases as a proximity of the detected object to the user decreases.

16. The method of claim 11, further comprising:
recognizing a face in the environment using one or more of the depth image data and the visible image data;
associating the face with an identity of a person; and
informing the user of the identity of the person.

17. The method of claim 16, further comprising:
assigning an identity earcon to the identity of the person; and
outputting the identity earcon to the user via the one or more transducers.

18. The method of claim 11, further comprising outputting a haptic navigation cue to the user via the one or more transducers.

19. The method of claim 11, further comprising, based on detecting the feature, displaying a visual navigation cue to the user via a display system of the head-mounted computing device, wherein the visual navigation cue is based on at least a three-dimensional location of feature in the environment.

20. A method for providing navigation assistance to a user in an environment via audio output in a head-mounted computing device, the method comprising:
receiving depth image data from the environment;
receiving visible image data from the environment;
using the depth image data and visible image data, generating a three-dimensional mesh of at least a portion of the environment;
using the three-dimensional mesh, detecting at least one feature in the environment;
when the head-mounted computing device is operating in a familiar navigation mode and based on detecting the feature, outputting a first audio navigation cue of the environment to the user via the one or more transducers;
when the head-mounted computing device is operating in the unfamiliar navigation mode and based on detecting the feature, outputting a second audio navigation cue of the environment to the user via the one or more transducers, wherein the second audio navigation cue differs from the first audio navigation cue; and
outputting one or more of the first audio navigation cue and the second audio navigation cue to the user in a manner that causes the user to perceive the cue as originating at a three-dimensional location of the feature.

* * * * *